United States Patent [19]

Da Col et al.

[11] Patent Number: 5,532,353

[45] Date of Patent: Jul. 2, 1996

[54] PROCESS FOR THE PREPARATION OF HALOGENATED β-LACTAM COMPOUNDS

[75] Inventors: Marco Da Col, Bologna; Leone Dall'Asta, Pavia; Irene Resta, Milan; Gianfranco Cainelli, Bologna; Michele Contento, Bologna; Mauro Panunzio, Bologna; Achille Umani Ronchi, Bologna, all of Italy

[73] Assignee: Biochimica Opos SpA, Milan, Italy

[21] Appl. No.: 58,714

[22] Filed: May 10, 1993

[30] Foreign Application Priority Data

May 11, 1992 [IT] Italy .................................. MI92A1125

[51] Int. Cl.⁶ .................................................. C07D 501/02
[52] U.S. Cl. ................................................ 540/215; 540/222
[58] Field of Search ............................... 540/215, 222, 540/221

[56] References Cited

U.S. PATENT DOCUMENTS 4,064,343  12/1977  Chauvette ........................... 540/215
5,043,439   8/1991  Kant et al. ........................... 540/215

FOREIGN PATENT DOCUMENTS

A-2218878  9/1974  France .
A-2259826  8/1975  France .
A-2218877  9/1994  France .

OTHER PUBLICATIONS

Chemical Abstracts, vol. 111.194375e, No. 21, 20 Nov. 1989, Columbus, Ohio, US.
The Journal Or Organic Chemistry, vol. 54, No. 20, 29 Sep. 1989, Washington, pp. 4962–4966 Vittorio Farina et al.
PCT Publication (WO 93/11132) (Nov. 27, 1992).

*Primary Examiner*—Nicholas Rizzo
*Attorney, Agent, or Firm*—Nikaido, Marmelstein, Murray & Oram

[57] ABSTRACT

There is described the preparation of halogenated β-lactam derivatives by introduction of a chlorine atom in the 3-position of the cephem nucleus starting from a 3-sulfonyloxycephem. Such starting materials are reacted with a chlorine ions donor in a basic medium.

22 Claims, No Drawings

PROCESS FOR THE PREPARATION OF HALOGENATED β-LACTAM COMPOUNDS

The present invention concerns a process for the preparation halogenated β-lactam derivatives.

More particularly, the present invention refers to a process for the introduction of a chlorine atom in the 3-position of the cephem nucleus by treatment of a 3-sulfonyloxy-3-cephem or of a mixture of $\Delta^2$ and $\Delta^3$ isomers with a chlorine ions donor.

The 3-chloro-3-cephem derivatives are antibiotics having a broad spectrum of activity. More particularly, the 7-(D-2-amino-2-phenylacetamido)-3-chloro-3-cephem-4-carboxylic acid, known under its International Non-Proprietary Name "cefaclor", is the active ingredient of orally active antibacterial pharmaceutical specialities.

It has now been surprisingly found that when a 3-sulfonyloxy-3-cephem, or a mixture of isomers $\Delta^2$ and $\Delta^3$, is subjected to the action of chlorine ions donor in the presence of a base, a nucleophilic substitution of the sulfonic group with the chlorine atom occurs, with consequent formation of a mixture of $\Delta^2$ and $\Delta^3$ isomers of a 3-chlorocephem.

The mixture of $\Delta^2$ and $\Delta^3$ isomers can be converted to a 3-chloro-3-cephem by oxydation to sulfoxide and subsequent reduction.

Thus, it is an object of the present invention to provide a process for the preparation of a mixture of isomers $\Delta^2$ and $\Delta^3$ of a 3-chlorocephem of formula (I)

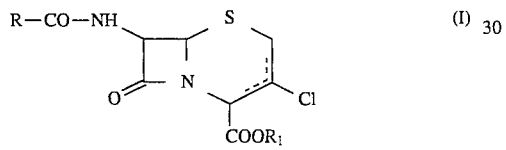

wherein

R is an alkyl group of from 1 to 6 carbon atoms, an haloalkyl group of from 1 to 3 carbon atoms, a cyanoalkyl group of from 1 to 3 carbon atoms, a phenyl, methylphenyl, nitrophenyl, methoxyphenyl, phenylthiomethyl, benzyl group or a substituted benzyl group having the structure

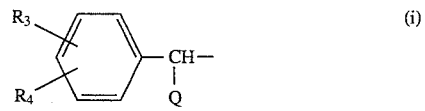

wherein $R_3$ and $R_4$, independently, represent hydrogen, an alkyl group of from 1 to 4 carbon atoms, an alcoxy group of from 1 to 4 carbon atoms, an halogen, a duly protected hydroxy group or a nitro group and Q is a duly protected hydroxy, carboxy or amino group; and $R_1$ represents a benzyl, 4-methoxybenzyl, 4-nitrobenzyl, diphenylmethyl, 2,2,2-trichloroethyl or t-butyl group, which comprises treating a 3-sulfonyloxy-3-cephem or a mixture of $\Delta^2$ and $\Delta^3$ isomers of formula (II)

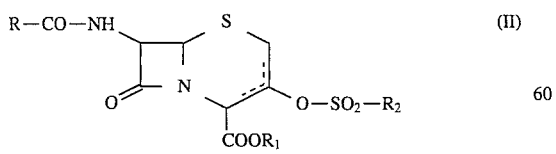

wherein R and $R_1$ have the above stated meaning and $R_2$ is an alkyl group containing from 1 to 6 carbon atoms, a phenyl group, a halophenyl group, a phenyl group substituted with an alkyl group containing from 1 to 3 carbon atoms, or a nitrophenyl, 2-pyridyl, 3-pyridyl, 4-pyridyl group, with a chlorine ions donor in an aprotic solvent and in the presence of an organic base or of an inorganic base, in the latter case such donor being a quaternary ammonium chloride.

In the present description, the definition of the compounds represented by the formulas (I) and (II) includes:

for the term "alkyl of from 1 to 6 carbon atoms", straight or branched-chain alkyl groups such as methyl, ethyl, n-propyl, iso-propyl, n-butyl, sec-butyl, n-amyl, isoamyl, n-hexyl and the like;

for the term "cyanoalkyl of from 1 to 3 carbon atoms", the cyanomethyl, 2-cyanoethyl, 3-cyanopropyl and 2-cyanopropyl groups;

for the term "alcoxy of from 1 to 4 carbon atoms", the methoxy, ethoxy, isopropoxy, n-butoxy groups and the like;

for the term "halogen", fluorine, chlorine, bromine and iodine;

for the term "haloalkyl of from 1 to 3 carbon atoms", a methyl, ethyl, propyl or isopropyl group which is substituted with a halogen atom as defined above;

for the term "protected amino group", the group $NH_2$ substituted with one of the urethane-like protecting groups commonly used in the peptide chemistry, for example the t-butoxycarbonyl (BOC), 2,2,2-trichloroethoxycarbonyl, benzyloxycarbonyl, p-nitrobenzyloxycarbonyl group or the same $NH_2$ group substituted with an enamine affording group, for example with ethyl acetoacetate, acetylacetone and the like or substituted with a triphenylmethyl (trityl) group.

In formulas (I) and (II), representative groups for the substituent RCO— are, in particular, phenylacetyl, 4-methylphenylacetyl, 3-ethylphenylacetyl, 4-isopropylphenylacetyl, 2-methylphenylacetyl, 4-chlorophenylacetyl, 4-nitrophenylacetyl, 4-bromophenylacetyl, 2,4-dichlorophenylacetyl, 3-bromophenylacetyl, 4-iodophenylacetyl, 2-fluorophenylacetyl, 3,4-dihydroxyphenylacetyl, 3-hydroxyphenylacetyl, 2,6-dimethoxyphenylacetyl, 3-ethoxyphenylacetyl, 4-methoxyphenylacetyl, 3,4-dimethoxyphenylacetyl, 4-t-butoxyphenylacetyl, 3-chloro-4-methylphenylacetyl, 3-nitrophenylacetyl, 4-methylmandeloyl, mandeloyl, 4-hydroxymandeloyl, 3-hydroxymandeloyl, 3-bromomandeloyl, 4-chloromandeloyl, 3-methyl-4-fluoromandeloyl, 2-fluoromandeloyl, 4-methoxymandeloyl, α-carboxyphenylacetyl, α-carboxy-4-methylphenylacetyl, α-carboxy-3,4-dichlorophenylacetyl, α-carboxy-4-hydroxyphenylacetyl, α-carboxy-2-methoxyphenylacetyl, α-carboxy-4-isopropoxyphenylacetyl, α-carboxy-3-hydroxyphenylacetyl, N-BOC-phenylglycyl, 4-hydroxy-N-BOC-phenylglycyl, 3-chloro-N-BOC-phenylglycyl, 3-hydroxy-N-BOC-phenylglycyl, 4-methoxy-N-BOC-phenylglycyl.

In formulas (I) and (II), representative groups for the substituent $R_1$ which are particularly useful are diphenylmethyl and 4-nitrobenzyl groups.

In formula (II), preferred groups for the substituent $R_2$ are methyl and 4-methylphenyl groups.

Preferred starting materials for the process of the present invention are:

diphenylmethyl 7-phenylacetamido-3-methanesulfonyloxy-3-cephem-4-carboxylate or a mixture of $\Delta^2$ and $\Delta^3$ isomers;

diphenylmethyl 7-phenylacetamido-3-(4-methylphenylsulfonyloxy)-3-cephem-4-carboxylate or a mixture of $\Delta^2$ and $\Delta^3$ isomers;

diphenylmethyl 7-phenylacetamido-3-(3-pyridylsulfonyloxy)-3-cephem-4-carboxylate or a mixture of $\Delta^2$ and $\Delta^3$ isomers;

4-nitrobenzyl 7-phenylacetamido-3-methanesulfonyloxy-3-cephem-4-carboxylate or a mixture of $\Delta^2$ and $\Delta^3$ isomers;

4-nitrobenzyl 7-phenylacetamido-3-(4-methylphenylsulfonyloxy)-3-cephem-4-carboxylate or a mixture of $\Delta^2$ and $\Delta^3$ isomers;

4-nitrobenzyl 7-phenylacetamido-3-(3-pyridylsulfonyloxy)-3-cephem-4-carboxylate or a mixture of $\Delta^2$ and $\Delta^3$ isomers;

diphenylmethyl 7-[D(–)-(N-BOC-α-amino)-phenylacetamido]-3-methanesulfonyloxy-3-cephem-4-carboxylate or a mixture of $\Delta^2$ and $\Delta^3$ isomers;

diphenylmethyl 7-[D(–)-(N-BOC-α-amino)-phenylacetamido]-3-(4-methylphenylsulfonyloxy)-3-cephem-4 -carboxylate or a mixture of $\Delta^2$ and $\Delta^3$ isomers;

diphenylmethyl 7-[D(–)-(N-BOC-α-amino)phenylacetamido]-3-(3-pyridylsulfonyloxy)-3-cephem-4 -carboxylate or a mixture of $\Delta^2$ and $\Delta^3$ isomers;

4-nitrobenzyl 7-[D(–)-(N-BOC-α-amino)phenylacetamido]-3-methanesulfonyloxy-3-cephem-4-carboxylate or a mixture of $\Delta^2$ and $\Delta^3$ isomers;

4-nitrobenzyl 7-[D(–)-(N-BOC-α-amino)phenylacetamido]-3-(4-methylphenylsulfonyloxy)-3-cephem-4-carboxylate or a mixture of $\Delta^2$ and $\Delta^3$ isomers;

4-nitrobenzyl 7-[D(–)-(N-BOC-α-amino)phenylacetamido]-3-(3-pyridylsulfonyloxy)-3-cephem-4 -carboxylate or a mixture of $\Delta^2$ and $\Delta^3$ isomers.

The compounds of formula (II) used as starting materials for the process of the present invention are, at least most of them, known in the literature. Scartazzani et al. in Helv. Chem. Acta 1975, 58, 2457, described them in detail and gave a method for their preparation. Compounds which are not described in the above document (formula II, $R_2$=4-, 3- or 2-pyridyl) may be easily prepared by reacting the 4-, 3- or 2-pyridylsulfonylchloride on the corresponding 3-hydroxycephem. Preferred starting materials are those in which R is a benzyl group a group (i) in which $R_3$, $R_4$ and Q have the above defined meaning.

According to the process of the present invention, the starting material (II), dissolved in an aprotic organic solvent, are treated with the chlorine ions donor agent in the presence of an organic or inorganic base and the reaction is followed by HPLC until the starting material disappears, at a temperature ranging between –5° C. and the refluxing temperature of the reaction mixture, preferably between 20° and 35° C.

As aprotic organic solvent, a hydrocarbon such as hexane, benzene or toluene; an ether such as methyl-t.butylether, tetrahydrofurane, dioxane; a chlorohydrocarbon such as dichloromethane, trichloromethane or 1,1,1-trichloroethane; or a polar solvent such as acetonitrile, N,N-dimethylformamide or N,N-dimethylacetamide; a ketone such as acetone or methyl isobutyl ketone may be used.

As chlorine ions donor, particularly, an inorganic chloride, a $Cl^-$ resin or a chloride of a quaternary ammonium compound may be used. Among the inorganic chlorides, every chloride may be used, sodium chloride and lithium chloride being preferred. Among the quaternary ammonium salts, tetramethylammonium chloride, tetraethylammonium chloride, trimethylbutylammonium chloride or triethylbutylammonium chloride are cited. Among the resins, Amberlyst A 26® (by Rohm and Haas) is particularly suitable.

The reaction is carried out in the presence of a base which may be used in catalytic or equimolecular amounts. Such a base may be inorganic, for example sodium or potassium carbonate, or organic. As an organic base, an amine or every organic substance having basic reaction is used. For example, trimethylamine, triethylamine, 1-methylmorpholine, diisopropylamine, tetramethylguanidine or tetraethylguanidine may be used.

Another base which may advantageously be used is the diisopropylethyllamine (Hunig base). Finally, such a base may be a basic resin, for example Amberlyst A 21® (by Rohm and Haas).

In the present specification and in the claims which follow, all the combinations $Cl^-$ donor/base/solvent are contemplated even though, in particular conditions, the reaction can give a result which is not very good. On the basis of the hereinbelow given specific examples it is possible to determine the best conditions to obtain a good product of formula (I), in good yields. For example, by using a protic solvent such as methanol, by-products of decomposition are obtained. A similar result is observed when gaseous $NH_3$ is used as a base. Conversely, reaction does not take place in the presence of a weak base such as aniline, pyridine or anisidine.

The reaction time depends on the temperature; normally, in the range between 20° and 35° C., the reaction is over after 3–15 hours and the compound of formula (I) is isolated according to the conventional techniques, for example by pouring the reaction mixture into cold acidic water, in order to neutralize the basic medium, and by extracting the product with a suitable solvent, for example ethyl acetate. By evaporation of the solvent and crystallization, the product of formula (I) is obtained in pure form.

The reaction of introduction of the chlorine atom, because of the basic medium in which it occurs, involves a shifting of the double bond from the 3- to the 2-position, so that the product thus obtained is a mixture of two isomeric compounds $\Delta^2$ and $\Delta^3$ in different proportions. In formula (I) the dotted lines between the position 2 and 3 indicate that the above formula represents a mixture of isomeric compounds $\Delta^2$ and $\Delta^3$.

The above mixture of formula (I) may be converted with excellent yields in the sole $\Delta^3$-compound by subjecting it to an oxydation and then to a reduction of the sulfoxide thus obtained.

Thus, according to another of its aspects, the present invention allows the passage from the 3-sulfonyl-3-cephem or from a mixture $\Delta^2$ and $\Delta^3$ of formula (II) to the corresponding 3-chloro-3-cephem in very good yields according to the reactions sequence depitched in Scheme 1.

Scheme 1

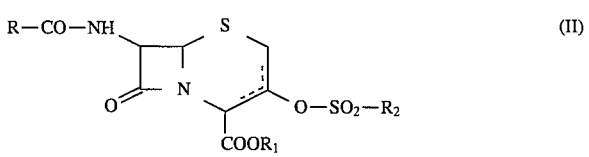

-continued
Scheme 1

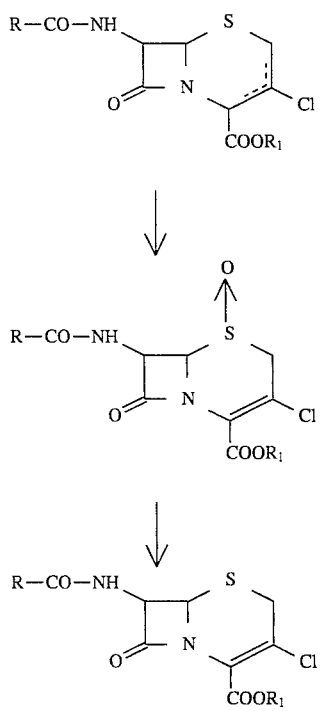

It is another object of the present invention to provide a global process for the preparation of a 3-chloro-3-cephem of formula (IV)

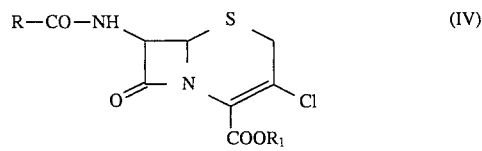

wherein R and $R_1$ are as defined above, which comprises (a) treating a 3-sulfonyloxy-3-cephem or a mixture of $\Delta^2$ and $\Delta^3$ isomers of formula (II)

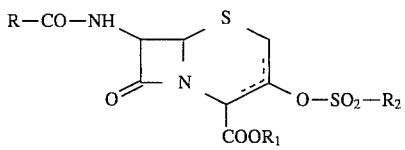

wherein R, $R_1$ and $R_2$ are as defined above, with a chlorine ions donor in an aprotic solvent and in the presence of an organic or inorganic base;

(b) subjecting the mixture of $\Delta^2$ and $\Delta^3$ isomers thus obtained of formula (I)

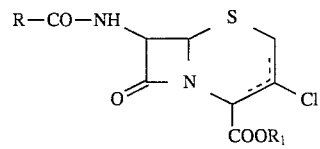

wherein R and $R_1$ are as defined above, to an oxydation with a peracid and, finally (c) subjecting the sulfoxide thus obtained of formula (III)

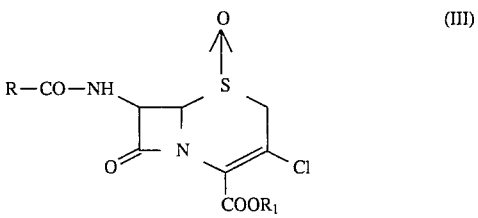

wherein R and $R_1$ are as defined above, to a reduction with phosphorus trichloride.

Step (a) is carried out as illustrated above in detail and the product obtained, consisting of a mixture of $\Delta^2$ and $\Delta^3$ isomers, may be purified or used in a raw state for the subsequent step (b).

In step (b) the product of formula (I), dissolved in an organic solvent, preferably a hydrocarbon or an ether as disclosed above, is treated with an oxydizing agent, preferably a peracid such as peracetic, perbenzoic, m-chloroperbenzoic, monoperphtalic acids. The sulfoxide of formula (III) thus obtained is isolated by simple filtration. Oxydation occurs, preferably, at a temperature of from 0° to 10° C. and in a solvent such as dioxane and tetrahydrofurane.

In step (c), the reduction of the sulfoxide (III) is carried out using an excess of phosphorus trichloride in an organic, preferably polar aprotic solvent such as dimethylformamide or dimethylacetamide at low temperature, preferably between −60° C. and −30° C. The product of formula (IV) which is obtained at the end of the reduction, is isolated according to known methods, preferably by precipitation with water. The reduction is practically quantitative, the final product being obtained in a pure state in a yield higher than 90%.

The compounds of formula (IV) obtained at the end of the global process (illustrated in the Scheme 1) are useful intermediates in the preparation of antibiotics. By hydrolysis of the ester on the carboxy group in position 4 there is directly obtained the free acid to be used in therapy. For example, starting from the diphenylmethyl or 4-nitrobenzyl esters of 7-[D(−)-α-(t-butoxycarbonylamino)-phenylacetamido]-3-methanesulfonyloxy-3-cephem-4-carboxylic acid or from a mixture of $\Delta^2$ and $\Delta^3$ isomers, the corresponding esters of 7-[D(−)-α-(t-butoxycarbonylamino)-phenylacetamido]-3-chloro-3 -cephem-4-carboxylic acid are obtained. By elimination of the ester group and liberation of the amine function, these compounds afford cefaclor.

The following examples illustrate the invention without, however, limiting it.

In order to render the reading of the tables easier, abreviations have been used. Their meaning is given hereinbelow.

don Cl⁻: chlorine ions donor
mol: equimolar amount
cat: catalytic amount
TEA: triethylamine
TEBA: triethylbutylammonium chloride
THF: tetrahydrofurane
iPr: isopropyl
Hunig: diisopropylethylamine
DMAP: dimethylaminopyridine

EXAMPLE 1

To 11.8 g (20 mmoles) of 4-nitrobenzyl 7-phenylacetamido-3-methanesulfonyloxy-3-cephem-4 -carboxylate in 70 ml of THF 5 g of lithium chloride and 0.3 ml of TEA are added. The disappearance of the starting product is followed by HPLC. After 5 hours the reaction mixture is poured in diluted hydrochloric acid containing ice and the product is extracted with ethyl acetate. The organic phase is dried on anhydrous sodium sulfate, then concentrated under reduced pressure. The 10.8 g of raw product thus obtained are triturated in methanol/ethyl ether. Thus, 8.6 g of 4-nitrobenzyl 7-phenylacetamido-3-chlorocephem-4-carboxylate are obtained as a mixture of $\Delta^2$ and $\Delta^3$ isomers (yield: 81.8%).

IR $\nu_{max}$ (KBr) cm$^{-1}$: 3260 (NH amide); 1770 (C=O β-lactam); 1720 (C=O ester; 1650 (C=O amide).

$^1$H-NMR (300 MHz, CDCl$_3$) δ 3.64 (ABq, CH$_2$-S, $\Delta^3$); 3.66 (m, benzyl CH$_2$, $\Delta^2$ and $\Delta^3$); 4.97 (d, J=1.6 Hz, 4-H, $\Delta^2$); 5.04 (d, J=4.8 Hz, 6-H, $\Delta^3$); 5.27 (d, J=4.1 Hz, 6-H, $\Delta^2$); 5.35 (m, ester CH$_2$, $\Delta^2$ and $\Delta^3$); 5.66 (dd, J=4.1 Hz and 8.8 Hz, 7-H, $\Delta^2$); 5.85 (dd, J=4.8 Hz and 8.8 Hz, 7-H, $\Delta^3$); 6.06 (d, J=8.8 Hz, NH, $\Delta^3$); 6.14 (d, J=8.8 Hz, NH, $\Delta^2$); 6.35 (d, J=1.5 Hz, =CH, $\Delta^2$); 7.24–8.25 (m, phenyl-H, $\Delta^2$ and $\Delta^3$).

EXAMPLE 2

To 5.47 g (10 mmoles) of a mixture of $\Delta^2$ and $\Delta^3$ isomers of 4-nitro benzyl 7-phenylacetamido-3-methanesulfonyloxycephem-4-carboxylate in 50 ml of THF 2.5 g of lithium chloride and 0.1 ml of N-methylmorfoline are added at room tempeature. After the disappearance of the starting product, the reaction mixture is poured in hydrochloric acid containing ice water, then extracted with ethyl acetate. The organic phase is dried on anhydrous sodium sulfate and concentrated under reduced pressure. The raw product is triturated with a methanol/ethyl ether mixture. Thus, 3.9 g of 4-nitrobenzyl 7-phenylacetamido-3-chlorocephem-4-carboxylate are obtained as a mixture of $\Delta^2$ and $\Delta^3$ isomers (yield: 80%).

EXAMPLES 3 TO 15

By operating as described in Examples 1 and 2 and reacting 4-nitro benzyl 7-phenylacetamido-3-methanesulfonyloxy-3-cephem-4-carboxylate or a mixture of $\Delta^2$ and $\Delta^3$ isomers with the appropriate chlorine ions donor in the presence of the base B, in a molar or catalytic amount, in the suitable solvent, the 4-nitrobenzyl 7-phenylacetamido-3-chlorocephem-4-carboxylate is obtained as a mixture of isomers $\Delta^2$ and $\Delta^3$ in the yield as shown in Table I.

TABLE I

| Example No. | Base (B) | don Cl$^-$ | Solvent | Yield* (II) |
|---|---|---|---|---|
| 3 | TEA cat | Amberlyst A 26 | THF | 80% |
| 4 | TEA cat | LiCl | THF | 82% |
| 5 | TEA cat | TEBA | CH$_2$Cl$_2$ | 82% |
| 6 | Na$_2$CO$_3$ mol | TEBA | THF | 80% |
| 7 | Hunig mol | TEBA | THF | 75% |
| 8 | Methyl-morpholine mol | TEBA | CH$_2$Cl$_2$ | 75% |
| 9 | (iPr)$_2$NH cat | LiCl | THF | 78% |
| 10 | [(CH$_3$)$_2$N]$_2$C—NH mol | LiCl | THF | 70% |
| 11 | TEA cat | LiCl | Acetone | 81% |
| 12 | TEA cat | LiCl | CH$_3$CN | 82% |
| 13 | DMAP cat | LiCl | THF | 55% |
| 14 | TEA mol | (CH$_3$)$_4$N$^+$Cl$^-$ | THF | 20% |
| 15 | Amberlyst A 21 | LiCl | THF | 80% |

*expressed as $\Delta^2$ + $\Delta^3$ isomers

EXAMPLE 16

To 5.7 8 g (10 mmoles) of diphenylmethyl 7-phenylacetamido-3-methanesulfonyloxy-3-cephem-4-carboxylate in 40 ml of THF, 2.5 g of lithium chloride and 0.2 ml of TEA are added at room temperature. After the disappearance of the starting material, the reaction mixture is poured in hydrochloric acid containing ice water. The product is extracted with ethyl acetate, the organic phase is dried on anhydrous sodium sulfate, then concentrated. The residue is crystallized from methanol/ether.

Thus, 4.1 g of diphenylmethyl 7-phenylacetamido-3-chloro-4-carboxylate are obtained as a mixture of $\Delta^2$ and $\Delta^3$ isomers (yield: 79.1%).

IR $\nu_{max}$ (KBr) cm$^{-1}$: 3260 (NH amide); 1770 (C=O β-lactam); 1720 (C=O ester; 1650 (C=O amide).

$^1$H-NMR (300 MHz, CDCl$_3$) δ 3.60 (ABq, CH$_2$-S, $\Delta^3$); 3.64 (m, benzyl CH$_2$, and $\Delta^3$); 5.0 (s, 4-H, $\Delta^2$); 5.02 (d, 6-H, $\Delta^3$); 5.19 (d, 6-H, $\Delta^2$); 5.58 (dd, 7-H, $\Delta^2$); 5.86 (dd, 7-H, $\Delta^3$); 6.34 (m, =CH, $\Delta^2$+NH, $\Delta^2$ and 6.90 (s, CH ester, $\Delta^2$); 6.99 (s, CH ester, $\Delta^3$) 7.2–7.4 (m, phenyl-H, $\Delta^2$ and $\Delta^3$).

EXAMPLES 17–20

By operating as described in Example 16 and reacting diphenylmethyl 7-phenylacetamido-3-methanesulfonyloxycephem-4 -carboxylate as a mixture of $\Delta^2$ and $\Delta^3$ isomers with the appropriate chlorine ions donor in the presence of the base B in the suitable solvent, diphenylmethyl 7-phenylacetamido-3-chlorocephem-4-carboxylate is obtained as a mixture of $\Delta^2$ and $\Delta^3$ isomers in the yields shown in Table II.

TABLE 2

| Example No. | Base (B) | don Cl$^-$ | Solvent | Yield* (II) |
|---|---|---|---|---|
| 17 | TEA cat | Amberlyst A 26 | THF | 81% |
| 18 | TEA cat | LiCl | TMF | 82% |
| 19 | TEA cat | TEBA | CH$_2$Cl$_2$ | 81.8% |
| 20 | Amberlyst A 21 | TEBA | CH$_2$Cl$_2$ | 80% |

*expressed as $\Delta^2$ + $\Delta^3$ isomers

EXAMPLE 21

(a) By operating as described in Example 1, 9 g of 4-nitrobenzyl phenylacetamido-3-chlorocephem-4-carboxylate are isolated as a mixture of $\Delta^2$ and $\Delta^3$ isomers.

(b) To the 9 g of the product thus obtained, dissolved in 50 ml of THF, 10 g of m-chloroperbenzoic acid, dissolved in 20 ml of THF are added at 0° C. After the disappearance of the starting product (control by HPLC), the precipitate is filtered, washed with ether and dried under vacuum. Thus, 8.5 g of nitrobenzyl 7-phenylacetamido-3-chloro-3-cephem-4-carboxylate 1-oxide are obtained (yield: 93.5%).

IR $\nu_{max}$ (KBr) cm$^{-1}$: 3280 (NH amide); 1785 (C=O β-lactam); 1725 (C=O ester; 1650 (C=O amide).

$^1$H-NMR (300 MHz, DMSO-d$_6$) δ 3.62 (ABq, 2H, benzyl CH$_2$); 4.03 (dd, 1H, J=18.4 Hz and 1.3 Hz, 2-H); 4.24 (d, 1H, J=18.4 Hz, 2-H); 5.01 (dd, 1H, J=4.9 Hz and 1.3 Hz, 6-H); 5.50 (ABt, 2H, CH$_2$ ester); 5.88 (dd, 1H, J=4.9 Hz and 7.9 Hz, 7-H); 7.3 (m, 5H, phenyl-H); 7.72 (d, 2H, phenyl-H); 8.27 (d, 2H, phenyl-H); 8.64 (d, 1H, J=7.9 Hz, NH).

(c) To 2.2 g (4 mmoles) of the product thus obtained in 25 ml of dimethylformamide, 8 mmoles of phosphorus trichloride are added at −50° C.

9

After the disappearance of the starting material, the reaction mixture is poured into water and the precipitate is filtered. The product thus obtained is triturated with methanol/ethyl ether and dried under vacuum. Thus, 1.9 g of 4-nitrobenzyl 7-phenylacetamido-3-chloro-3-cephem-4-carboxylate are obtained (yield: 86.7%).

IR $\nu_{max}$ (KBr) cm$^{-1}$: 3260 (NH amide); 1770 (C=O β-lactam); 1730 (C=O ester; 1650 (C=O amide).

$^1$H-NMR (300 MHz, CDCl$_3$) δ 3.63 (ABq, 2H, S-CH$_2$); 3.65 (ABq, 2H, CH$_2$ benzyl); 5.03 (d, 1H, J=4.6 Hz, 6-H); 5.36 (ABq, 2H, CH$_2$ ester); 5.85 (dd, 1H, J=4.6 Hz and 9.1 Hz, 7-H); 6.19 (d, 1H, J=9.1 Hz, NH); 7.3 (m, 5H, phenyl-H); 7.56 (d, 2H, phenyl-H); 8.23 (d, 2H, phenyl-H).

EXAMPLE 22

(a) By operating as described in Example 16, 4.1 g of diphenylmethyl 7-phenylacetamido-3-chlorocephem-4-carboxylate are obtained as a mixture of Δ$^2$ and Δ$^3$ isomers.

(b) To 2.6 g (5 mmoles) of the product obtained in (a), dissolved in 50 ml of THF, 2.5 g of m-chloroperbenzoic acid are added at 0° C. After the disappearance of the starting material (control by HPLC), the precipitate is filtered, washed with ether and dried under vacuum Thus, 2.2 g of diphenylmethyl 7-phenylacetamido-3-chloro-3-cephem-4-carboxylate 1-oxide are obtained (yield: 80%).

IR $\nu_{max}$ (KBr) cm$^{-1}$: 3280 (NH amide); 1780 (C=O β-lactam); 1730 (C=O ester; 1650 (C=O amide).

$^1$H-NMR (300 MHz, DMSO-d$_6$) δ 3.65 (ABq, 2H, benzyl CH$_2$); 4.13 (ABq, 2H, S-CH$_2$); 5.02 (d, 1H, J=4.8 Hz, 6-H); 5.9 (dd, 1H, J=7.8 Hz and 4.8 Hz, 7-H); 7.01 (s, 1H, CH ester); 7.35 (m, 15H, phenyl-H); 8.65 (d, 1H, J=7.8 Hz, NH).

(c) To the 2.2 g (4.1 mmoles) of the product obtained in (b), dissolved in N,N-dimethylformamide, 8.2 mmoles of phosphorus trichloride are added at −50° C. After verifying by HPLC the disappearance of the starting product, the reaction mixture is poured into water, the precipitate is filtered and dried under vacuum. Thus, 2 g of diphenylmethyl 7-phenylacetamido-3-chloro-3-cephem-4-carboxylate are obtained (yield: 94.7%).

IR $\nu_{max}$ (KBr) cm$^{-1}$: 3270 (NH amide); 1770 (C=O β-lactam); 1720 (C=O ester; 1650 (C=O amide).

$^1$H-NMR (300 MHz, CDCl$_3$) δ 3.60 (ABq, 2H, S-CH$_2$); 3.64 (ABq, 2H, benzyl CH$_2$); 5.01 (d, 1H, J=4.8 Hz, 6-H); 5.83 (dd, 1H, J=4.8 Hz and 9.0 Hz, 7-H); 6.13 (d, 1H, J=9.0 Hz, NH); 6.97 (s, 1H, CH ester); 7.2–7.4 (m, 15H, phenyl-H).

We claim:

1. Process for the preparation of a 3-chlorocephem, as a mixture of Δ$^2$ and Δ$^3$ isomers, of formula (I)

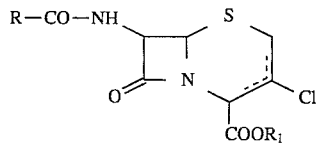

wherein

—R is an alkyl group of from 1 to 6 carbon atoms, a haloalkyl of from 1 to 3 carbon atoms, a cyanoalkyl of from 1 to 3 carbon atoms, a phenyl, methylphenyl, nitrophenyl, methoxyphenyl, phenylthiomethyl, benzyl, or a substituted benzyl group having the structure (i)

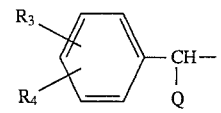

wherein R$_3$ and R$_4$, independently, represent hydrogen, alkyl of from 1 to 4 carbon atoms, alcoxy of from 1 to 4 carbon atoms, halogen, hydroxy or a nitro group and Q is a hydroxy or a protected carboxyl group or an amino group protected by an urethane-like protecting group selected from the group consisting of t-butoxycarbonyl, 2,2,2-trichloroethoxycarbonyl, benzyloxycarbonyl and p-nitrobenzyloxycarbonyl, by an enamine affording compound selected from the group consisting of ethylacetoacetate and acetylacetone or by a trityl group; and —R$_1$ represents benzyl, 4-methoxybenzyl, 4-nitrobenzyl, diphenylmethyl, 2,2,2-trichloroethyl or t-butyl, which comprises treating a 3-sulfonyloxy-3-cephem or a mixture of Δ$^2$ and Δ$^3$ isomers of formula (II)

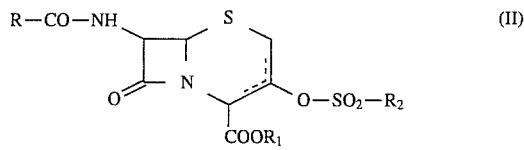

wherein R and R$_1$ are as defined above and R$_2$ is an alkyl group containing from 1 to 6 carbon atoms, a phenyl, halophenyl group or a phenyl group substituted with an alkyl containing from 1 to 3 carbon atoms or a nitrophenyl, 2-pyridyl, 3-pyridyl or 4-pyridyl group, with a chlorine ions donor in an aprotic solvent and in the presence of a base.

2. A process according to claim 1 wherein lithium chloride, sodium chloride, tetramethylammonium chloride, tetraethylammonium chloride, trimethylbutylammoniumchloride or a Cl$^-$ resin is used as chlorine ions donor.

3. A process according to claim 1 wherein trimethylamine, triethylamine, 4-methylmorpholine, diisopropylamine, diisopropylethylamine, tetramethylguanidine or tetraethylguanidine is used as organic base.

4. A process according to claim 1, wherein a quaternary ammonium chloride in the presence of an inorganic base is used as chlorine ions donor.

5. A process according to claim 1 wherein sodium carbonate or potassium carbonate is used as inorganic base.

6. A process according to claim 1 wherein the reaction temperature is in the range between −5° C. and the refluxing temperature of the reaction mixture.

7. A process according to claim 6 wherein said reaction temperature is in the range of from 20° and 35° C.

8. A process according to claim 1 wherein the reaction is carried out in an aprotic solvent selected from the group consisting of hydrocarbons, ethers, chlorohydrocarbons and polar solvents.

9. A process according to claim 8 wherein said hydrocarbon is selected from the group consisting of hexane, benzene and toluene.

10. A process according to claim 8 wherein said ether is selected from the group consisting of methyl-t.butylether, tetrahydrofurane and dioxane.

11. A process according to claim 8 in which said chlorohydrocarbon is selected from the group consisting of dichloromethane, trichloromethane or 1,1,1-trichloroethane.

12. A process according to claim 8 wherein said polar solvent is selected from the group consisting of acetonitrile, N,N-dimethylformamide and N,N-dimethylacetamide.

13. A process according to claim 8 wherein said aprotic solvent is a ketone selected from the group consisting of acetone and isobutylmethylketone.

14. A process according to claim 1 wherein a compound of formula (II) according to claim 1, in which R is selected from the group consisting of benzyl and a substituted benzyl of structure (i)

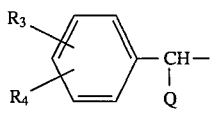

in which $R_3$ and $R_4$, independently, represent hydrogen, an alkyl of from 1 to 4 carbon atoms, an alcoxy of from 1 to 4 carbon atoms, a halogen, a hydroxy group or a nitro group and Q is a hydroxy or a protected carboxy group or an amino group protected by an urethane-like protecting group selected from the group consisting of t-butoxycarbonyl, 2,2,2-trichloroethoxycarbonyl, benzyloxycarbonyl and p-nitrobenzyloxycarbonyl, by an enamine affording compound selected from the group consisting of ethylacetoacetate and acetylacetone or by a trityl group is used as starting material.

15. A process according to claim 1, wherein a compound of formula (II), in which $R_1$ is a diphenylmethyl or a 4-nitrobenzyl group, is used as starting material.

16. A process according to claim 1, wherein a compound of formula (II), in which $R_2$ is methyl or 4-methylphenyl, is used as starting material.

17. A process according to claim 1, wherein the starting compound is selected from the group consisting of:
 diphenylmethyl 7-phenylacetamido-3-methanesulfonyloxy-3-cephem-4-carboxylate or a mixture of $\Delta^2$ and $\Delta^3$ isomers;
 diphenylmethyl 7-phenylacetamido-3-(4-methyl-phenylsulfonyloxy)-3-cephem-4-carboxylate or a mixture of $\Delta^2$ and $\Delta^3$ isomers;
 diphenylmethyl 7-phenylacetamido-3-(3-pyridylsulfonyloxy)-3-cephem-4-carboxylate or a mixture of $\Delta^2$ and $\Delta^3$ isomers;
 4-nitrobenzyl 7-phenylacetamido-3-methanesulfonyloxy-3-cephem-4-carboxylate or a mixture of $\Delta^2$ and $\Delta^3$ isomers;
 4-nitrobenzyl 7-phenylacetamido-3-(4-methyl-phenylsulfonyloxy)-3-cephem-4-carboxylate or a mixture of $\Delta^2$ and $\Delta^3$ isomers;
 4-nitrobenzyl 7-phenylacetamido-3-(3-pyridylsulfonyloxy)-3-cephem-4-carboxylate or a mixture of $\Delta^2$ and $\Delta^3$ isomers;
 diphenylmethyl 7-[D(−)-(n-BOC-α-amino)-phenylacetamido]-3-methanesulfonyloxy-3-cephem-4-carboxylate or a mixture of $\Delta^2$ and $\Delta^3$ isomers;
 diphenylmethyl 7-[D(−)-(N-BOC-α-amino)-phenylacetamido]-3-(4-methyl-phenylsulfonyloxy)-3-cephem-4-carboxylate or a mixture of $\Delta^2$ and $\Delta^3$ isomers;
 diphenylmethyl 7-[D(−)-(N-BOC-α-amino)phenylacetamido]-3-(3-pyridyl sulfonyloxy)-3-cephem-4-carboxylate or a mixture of $\Delta^2$ and $\Delta^3$ isomers;
 4-nitrobenzyl 7-[D(−)-(N-BOC-α-amino)phenylacetamido]-3-methanesulfonyloxy-3-cephem-4-carboxylate or a mixture of $\Delta^2$ and $\Delta^3$ isomers;
 4-nitrobenzyl 7-[D(−)-(N-BOC-α-amino)phenylacetamido]-3-(4-methyl-phenylsulfonyloxy)-3-cephem-4-carboxylate or a mixture of $\Delta^2$ and $\Delta^3$ isomers and;
 4-nitrobenzyl 7-[D(−)-(N-BOC-α-amino)phenylacetamido]-3-(3-pyridyl sulfonyloxy)-3-cephem-4-carboxylate or a mixture of $\Delta^2$ and $\Delta^3$ isomers.

18. Process for the preparation of a 3-chloro-3-cephem of formula (IV)

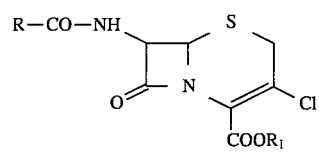

wherein R is an alkyl group of from 1 to 6 carbon atoms, a haloalkyl of from 1 to 3 carbon atoms, a cyanoalkyl of from 1 to 3 carbon atoms, a phenyl, methylphenyl, nitrophenyl, methoxyphenyl, phenylthiomethyl, benzyl or a substituted benzyl group having the structure (i)

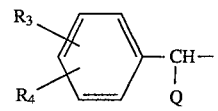

wherein $R_3$ and $R_4$, independently, represent hydrogen, alkyl of from 1 to 4 carbon atoms, alcoxy of from 1 to 4 carbon atoms, halogen, hydroxy or a nitro group and Q is a hydroxy or a protected carboxy group or an amino group protected by an urethane-like protecting group selected from the group consisting of t-butoxycarbonyl, 2,2,2-trichloroethoxycarbonyl, benzyloxycarbonyl and p-nitrobenzyloxycarbonyl, by an enamine affording compound selected from the group consisting of ethylacetoacetate and acetylacetone or by a trityl group; and $R_1$ represents benzyl, 4-methoxybenzyl, 4-nitrobenzyl, diphenylmethyl, 2,2,2-trichloroethyl or t-butyl, which comprises:

(a) treating a 3-sulfonyloxy-3-cephem or a mixture of $\Delta^2$ and $\Delta^3$ isomers of formula (II)

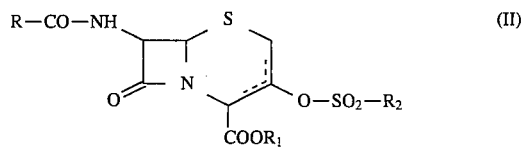

wherein R and $R_1$ are as defined above and $R_2$ is an alkyl group containing from 1 to 6 carbon atoms, a phenyl, halophenyl group or a phenyl group substituted with an alkyl containing from 1 to 3 carbon atoms or a nitrophenyl, 2-pyridyl, 3-pyridyl or 4-pyridyl group, with a chlorine ions donor in an aprotic solvent and in the presence of an organic or inorganic base;

(b) subjecting the mixture of $\Delta^2$ and $\Delta^3$ isomers thus obtained of formula (I)

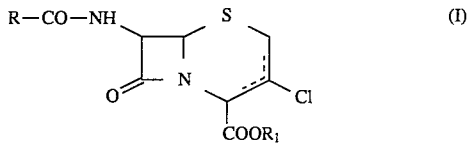

wherein R and $R_1$ are as defined above, to an oxidation with a peracid and, then (c) subjecting the sulfoxide thus obtained of formula (III)

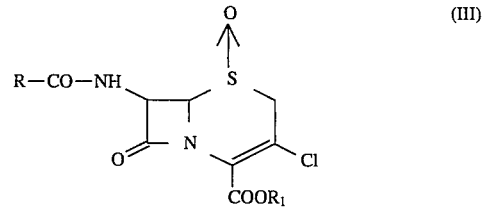

wherein R and $R_1$ are defined above to a reduction with phosphorus trichloride.

19. A process according to claim 18 wherein the step (a) is carried out according to one of claims 1 to 8.

20. A process according to claim 18 wherein peracetic acid, perbenzoic acid, m-chloroperbenzoic acid or monoperphtalic acid is used as peracid in step (b).

21. A process according to claim 18 wherein the reduction with phosphorus trichloride is carried out in a polar aprotic solvent at a temperature of from −70° to +20° C.

22. A process according to claim 21, wherein said reduction is carried out in a polar aprotic solvent at a temperature of from −60° to −30° C.

* * * * *